(12) United States Patent
Cooper

(10) Patent No.: US 6,780,391 B1
(45) Date of Patent: Aug. 24, 2004

(54) METHOD OF PRODUCING SURGICAL GRADE CALCIUM SULPHATE

(75) Inventor: John Joseph Cooper, Crewe (GB)

(73) Assignee: Biocomposites Limited (GB)

( * ) Notice: Subject to any disclaimer, the term of this patent is extended or adjusted under 35 U.S.C. 154(b) by 0 days.

(21) Appl. No.: 10/031,501

(22) PCT Filed: Jul. 5, 2000

(86) PCT No.: PCT/GB00/02584

§ 371 (c)(1),
(2), (4) Date: Jan. 15, 2002

(87) PCT Pub. No.: WO01/05706

PCT Pub. Date: Jan. 25, 2001

(30) Foreign Application Priority Data

Jul. 16, 1999 (GB) .............................................. 9916601

(51) Int. Cl.⁷ ................................................ C01F 11/46
(52) U.S. Cl. ..................................................... 423/555
(58) Field of Search ......................................... 423/555

(56) References Cited

U.S. PATENT DOCUMENTS 4,360,386 A    11/1982  Bounini ...................... 106/110
5,248,487 A  *  9/1993  Bold et al. ................... 473/171
5,281,265 A     1/1994  Liu ............................. 106/35
5,756,127 A     5/1998  Grisoni et al. .............. 424/489

FOREIGN PATENT DOCUMENTS

EP    0370793 A1    5/1990    ......... C04B/11/024
SU    345098    *    7/1972    ................. 423/555

OTHER PUBLICATIONS

Murakami et al. "Studies on the Hydration of Natural Anhydrite" *Gypsum and Lime* (1953), pp. 350–357.*
Copy of International Search Report dated Nov. 15, 2000, pp. 1–2 for PCT/GB00/02584.
Abstract, Derwent Publications Ltd., Jul. 18, 1977, Database WPI Abstract No. 1977–56914Y.

* cited by examiner

*Primary Examiner*—Wayne A. Langel
(74) *Attorney, Agent, or Firm*—Watts Hoffman Co., L.P.A.

(57) ABSTRACT

A method of producing surgical grade calcium sulphate suitable for use as resorbable osteoconductive bone void filler material. The method comprising forming an initial calcium sulphate di-hydrate from synthetic constituents; dehydrating the initial calcium sulphate di-hydrate to form calcium sulphate anhydrite; and subsequently rehydrating the calcium sulphate anhydrite and allowing subsequent calcium sulphate di-hydrate to crystallize out.

47 Claims, No Drawings

METHOD OF PRODUCING SURGICAL GRADE CALCIUM SULPHATE

The present application claims priority from PCT/GB00/02584 filed Jul. 5, 2000.

This invention concerns a method of producing surgical grade calcium sulphate and particularly but not exclusively a method of producing a resorbable osteoconductive bone void filler material.

Plaster of paris (hemi-hydrate calcium sulphate) is known to be suitable for use as a filler for bone defects. This material provides a number of required characteristics and does not produce any significant undesirable reaction within a body. Traditionally plaster of paris is produced from naturally occurring gypsum. This often has associated undesirable impurities. For medical applications and particularly for implantation high purity materials are obviously needed. Whilst it is possible for calcium sulphate to be produced synthetically, conventional techniques produce a material which has a high surface area which thus has a high water demand and therefore produces a low strength material when set. Such set material has a high dissolution rate and too short a residence time when implanted.

Plaster of paris, or more accurately calcium sulphate, has two modes of use as a bone filler. The first is in the di-hydrate form, usually as pellets which can be placed in a bone void. The second is as a hemi-hydrate powder which can be made up with water into a paste, which paste is mouldable to a required shape. Such materials are usable in the fields of orthopaedic, dental and maxillofacial surgery. Hemi-hydrate calcium sulphate has two forms. The first $\alpha$ is produced by hydrothermal treatment of the di-hydrate. The second $\beta$ is produced by dry heat calcination. This latter form tends to have a low density, a higher water demand and therefore a lower strength and a faster dissolution rate than the $\alpha$ form.

According to the present invention there is provided a method of producing surgical grade calcium sulphate, the method comprising forming an initial calcium sulphate di-hydrate from synthetic constituents; dehydrating the initial calcium sulphate di-hydrate to form calcium sulphate anhydrite; and subsequently rehydrating the calcium sulphate anhydrite and allowing subsequent calcium sulphate di-hydrate to crystallise out.

The subsequent di-hydrate may be used as a solid material bone filler and may be formed into pellets. The crystallised subsequent calcium sulphate di-hydrate may be ground prior to forming into pellets.

Alternatively, the subsequent calcium sulphate di-hydrate may be calcined to form calcium sulphate hemi-hydrate, which material can be mixed with water or a salt solution to form a settable paste.

The calcining may be hydrothermal to form a calcium sulphate hemi-hydrate, and may be carried out in an autoclave. The calcining may be carried out at a pressure of 1–6 bar, and desirably 2–3 bar. The calcining is preferably carried out for a half to five hours, and desirably one to two hours.

Alternatively, the calcining may be carried out in dry heat conditions. The calcining may be carried out at a temperature of 70–200° C. and desirably at 150–175° C., and for a period of a half to six hours and desirably one to two hours.

Following calcining, the calcium sulphate hemi-hydrate is preferably ground to a powder, and desirably with a particle size of less than 150 microns.

The initial calcium sulphate di-hydrate may be formed by mixing soluble calcium and sulphate salts such that calcium sulphate precipitates out. The di-hydrate thus formed may be washed, and subsequently filtered, crushed and/or dried.

The calcium salt may be a chloride or nitrate. The sulphate may be a sodium, potassium or ammonium salt. The calcium and sulphate salts are preferably provided in a substantially equal molecular ratio.

Alternatively the initial calcium sulphate di-hydrate may be formed from neutralising lime with sulphuric acid.

The dehydration of the initial calcium sulphate di-hydrate preferably takes place within a temperature range 110–350° and desirably at less than 300° C., to form soluble calcium sulphate anhydrite. Alternatively the dehydration may take place at a temperature above 350° C. to form insoluble anhydrite.

The dehydration of the initial calcium sulphate di-hydrate by the application of heat may take place in an open container, or in a closed container, or hydrothermally in the presence of steam.

The rehydration of the calcium sulphate anhydrite preferably takes place immediately following dehydration. The calcium sulphate anhydrite is preferably fully immersed in water or an aqueous solution for rehydration.

The rehydration may take place in water or a dilute salt solution. The salt solution may comprise succinic acid or a potassium sulphate solution, with a concentration of less than 1% and desirably substantially 0.1%.

Finely powdered calcium sulphate di-hydrate may be added to be present during rehydration such that the powdered calcium sulphate acts as crystal seeds, and the addition may be in the order of 5 g per liter of water. For soluble anhydrite the rehydration preferably takes less than five days, and for insoluble anhydrite preferably more than five days.

The subsequent calcium sulphate di-hydrate is preferably dried following crystallisation. Alternatively, if it is to be autoclaved to form $\alpha$ hemi-hydrate it may be held in a damp condition.

Examples of the present invention will now be described by way of example only.

EXAMPLE 1

4 moles of analytical grade potassium sulphate were dissolved in 2 l of deionised water. The resulting solution was added to a solution of 4 moles calcium nitrate in 2 l of deionised water. The precipitate so formed was washed free of all nitrate and filtered on a Buchner Funnel followed by a further wash on filter with 100 ml of deionised water. The resultant filter cake was dried at 40° C. Its BET SSA (specific surface area measurement) was determined as 0.61 m$^2$/gm.

500 gms of this calcium sulphate di-hydrate filter cake were lightly crushed, put into a 2 l borosilicate glass beaker, and placed in an oven at 200° C. for 24 hours. On removal from the oven, 500 mls of deionised water—were added immediately to the beaker ensuring that all of the powder was immersed. This was allowed to soak for a period of 3 days, and then all supernatant liquid was drained away.

The resulting di-hydrate had a BET SSA of 0.06 m$^2$/gm. This coarse textured, granular, recrystallised di-hydrate was now placed in a stainless steel tray and autoclaved at 2.5 bar for a period of 2 hours. The $\alpha$ hemi-hydrate so formed was dried at 110° C. for half hour prior to crushing in a pestle and mortar to pass a 150 micron mesh sieve.

The material so formed could be blended with 0.35 parts of water to form an easily workable and mouldable paste which became firm after 6 minutes and set to a hard, dense mass soon after.

This material blended with 0.35 parts of a 0.5% potassium sulphate solution formed an easily workable and mouldable paste which became firm after 3 minutes, and set to a hard dense mass soon after.

EXAMPLE 2

2 moles of analytical grade calcium carbonate was added slowly and with gentle agitation to 2 L of 1N analytical grade sulphuric acid in a 3 liter glass beaker. When the effervescence has subsided and the pH of the resulting suspension was substantially neutral, pH=7.0, the suspended mass in its container was heated in an autoclave to a temperature of 130° C. and maintained at that temperature for 3 hours. After cooling, the precipitated calcium sulphate was allowed to soak in the supernatant for a period of 3 days and then all supernatant liquid was drained away. This powder was treated hydrothermally as in Example 1 above to produce an α hemi-hydrate.

EXAMPLE 3

500 gms of the precipitated calcium sulphate di-hydrate from Example 1 were put into a glass beaker, which was placed in an oven at 200° C. for 24 hours. On removal from the oven, 500 mls of 0.1% succinic acid solution were added to the beaker, ensuring that all of the powder was immersed. This was soaked for 16 hours, at which time the supernatant liquid was drained away to reveal a coarse textured recrystallised gypsum powder.

This powder was treated hydrothermally as in Example 1 above, followed by drying and crushing.

The resulting α hemi-hydrate was blended with 0.45 parts of water to form a paste which became firm after 6 minutes and set to a hard, dense mass soon after.

EXAMPLE 4

500 gms of the precipitated calcium sulphate di-hydrate from Example 2 were calcined in an oven at 400° C. for 2 hours. The anhydrite so formed was the orthorhombic or so called dead burned variety. This was removed from the oven, immersed in deionised water and allowed to soak for a period of 14 days. The supernatant liquid was drained away to reveal a coarse, gritty recrystallised gypsum powder. This was hydrothermally treated in an autoclave for 2½ hours at 1.7 bar. The resulting α hemi-hydrate was dried at 110° C. and crushed to pass a 125 micron mesh sieve. This gave a material which was blended with 0.38 parts of sterile, deionised water to form a mouldable paste which became firm 5 minutes after mixing, and set to a hard mass soon after.

EXAMPLE 5

Recrystallised di-hydrate prepared according to Example 1 was dried at 40° C. overnight. The dried material was crushed to pass a 150 micron mesh sieve and the resulting fine powder was heated in a shallow stainless steel tray at a depth of 2 cm for 2 hours at 165° C. The hemi-hydrate so formed was of the β variety, and was blended with 0.65 parts of sterile deionised water to form a mouldable paste which set to give a firm mass.

EXAMPLE 6

500 gms of the precipitated calcium sulphate di-hydrate from Example 1 were put into a glass beaker, which was placed in an oven at 150° C. for 40 minutes. On removal from the oven, the resultant β hemi-hydrate was added to 600 ml of deionised water and mixed to form a fluid mass. This was poured into a shallow stainless steel tray and allowed to re-hydrate and set. The following day the set gypsum in the stainless steel tray was put into an oven at 250° C. for 20 hours to allow for complete dehydration. The resulting calcium sulphate anhydrite was covered with deionised water and allowed to soak for a period of 4 days and then all supernatant liquid was drained away to reveal a coarse textured recrystallised gypsum powder. This powder was treated hydrothermally as in Example 1 above to produce an α hemi-hydrate.

SUMMARY

Examples 1 and 2 show alternative means of precipitating and subsequently dehydrating the initial calcium sulphate di-hydrate.

Example 4 shows that the insoluble anhydrite requires a much longer crystallisation time than the soluble variety. Example 5 shows the use of dry heat calcination to produce the β hemi-hydrate. It has been found that using a salt for the rehydration speeds up the process, as is illustrated in Example 3. Finely powdered gypsum may be added to act as crystal seeds.

Example 6 shows that the synthetic precipitated calcium sulphate di-hydrate can first be formed into a hemi-hydrate followed by re-hydration with a minimum quantity of water to form a set mass of di-hydrate. This set di-hydrate can then be dehydrated and recrystallised as previously described.

The above examples describe production of calcium sulphate hemi-hydrate which can be formed into a paste. The α hemi-hydrate thus formed can be blended with 0.30 to 0.40 parts water or saline solution to give a mouldable paste which sets to a firm mass. The β hemi-hydrate requires 0.55 to 0.70 parts water to form an appropriate paste.

If the calcium sulphate is required to be used in a pellet form, the calcination from the di-hydrate to the hemi-hydrate is not required. The subsequent di-hydrate would be ground or crushed and formed into pellets of an appropriate size.

There is thus described a method of producing surgical grade calcium sulphate which combines the advantages of the synthetic route with the characteristics encountered with naturally occurring gypsum. The method is relatively straightforward and can thus be readily reproduced, and without significant extra costs. The calcium sulphate produced by the methods herein described can provide an improved delivery means for the controlled release of medicaments into the body by virtue of their high chemical and phase purity compared to naturally occurring calcium sulphate. This provides for a more consistent and predictable rate of dissolution of the calcium sulphate and release of the medicament contained therein.

Various modifications may be made without departing from the scope of the invention. For example, the initial di-hydrate may be formed by neutralising lime with sulphuric acid. Other materials such as calcium chloride or sodium sulphate, may be used to form the initial calcium sulphate. Other salts may be used during the process as is required. Other conditions may he applicable to the dehydration, rehydration or calcining.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. A method of producing surgical grade calcium sulphate characterised in that the method comprises: forming an initial calcium sulphate di-hydrate from synthetic constituents; dehydrating the initial calcium sulphate di-hydrate to form calcium sulphate anhydrite; and subsequently rehydrating the calcium sulphate anhydrite by immersing in an aqueous solution selected from the group consisting water and a salt solution where the concentration of salt in solution is less than 1% and allowing subsequent calcium sulphate di-hydrate to crystallise out.

2. A method according to claim 1, characterised in that the subsequent di-hydrate is used as a solid material bone filler.

3. A method according to claim 1, characterised in that the subsequent di-hydrate is formed into pellets.

4. A method according to claim 3, characterised in that the crystallized subsequent calcium sulphate di-hydrate is ground prior to forming into pellets.

5. A method according to claim 1, characterised in that the subsequent calcium sulphate di-hydrate is calcined to form calcium sulphate hemi-hydrate.

6. A method according to claim 5, characterised in that the calcium sulphate hemi-hydrate is mixed with water to form a settable paste.

7. A method according to claim 5, characterised in that the calcium sulphate hemi-hydrate is mixed with a salt solution to form a settable paste.

8. A method according to claim 5, characterised in that the calcining is hydrothermal to form α calcium sulphate hemi-hydrate.

9. A method according to claim 8, characterised in that the calcining is carried out in an autoclave.

10. A method according to claim 9, characterised in that the calcining is carried out at a pressure of 1–6 bar.

11. A method according to claim 10, characterised in that the calcining is carried out at 2–3 bar.

12. A method according to claim 5, characterised in that the calcining is carried out in dry heat conditions.

13. A method according to claim 12, characterised in that the calcining is carried out at a temperature of 70–200° C.

14. A method according to claim 13, characterised in that the calcining is carried out at 150–175° C.

15. A method according to claim 8, characterised in that the calcining is carried out for a period of a half to six hours.

16. A method according to claim 15, characterised in that the calcining is carried out for one to two hours.

17. A method according to claim 5, characterised in that following calcining, the calcium sulphate hemi-hydrate is ground to a powder.

18. A method according to claim 17, characterised in that the powder has particle size of less than 150 microns.

19. A method according to claim 1, characterised in that the initial calcium sulphate di-hydrate is formed by mixing soluble calcium and sulphate salts such that calcium sulphate precipitates out.

20. A method according to claim 19, characterised in that the initial di-hydrate thus formed is washed, and subsequently filtered, crushed and/or dried.

21. A method according to claim 19, characterised in that the calcium salt is a chloride.

22. A method according to claim 19, characterised in that the calcium salt is a nitrate.

23. A method according to claim 19, characterised in that the sulphate is a sodium salt.

24. A method according to claim 19, characterised in that the sulphate is a potassium salt.

25. A method according to claim 19, characterised in that the sulphate is an ammonium salt.

26. A method according to claim 19, characterised in that the calcium and sulphate salts are provided in a substantially equal molecular ratio.

27. A method according to claim 1, characterised in that the initial calcium sulphate di-hydrate is formed from neutralising lime with sulphuric acid.

28. A method according to claim 1, characterised in that the dehydration of the initial calcium sulphate di-hydrate takes place within a temperature range 110–350° C.

29. A method according to claim 28, characterised in that the dehydration of the initial calcium sulphate di-hydrate takes place at less than 300° C.

30. A method according to claim 1, characterised in that the dehydration of the initial calcium sulphate di-hydrate takes place at a temperature above 350° C. to form insoluble anhydrite.

31. A method according to claim 30, characterised in that the rehydration takes more than five days.

32. A method according to claim 1, characterised in that the dehydration of the initial calcium sulphate di-hydrate by the application of heat takes place in an open container.

33. A method according to claim 1, characterised in that the dehydration of the initial calcium sulphate di-hydrate by the application of heat takes place in a closed container.

34. A method according to claim 1, characterised in that the dehydration of the initial calcium sulphate di-hydrate by the application of heat takes place hydrothermally in the presence of steam.

35. A method according to claim 1, characterised in that the rehydration of the calcium sulphate anhydrite takes place immediately following dehydration.

36. A method according to claim 1, characterised in that the calcium sulphate anhydrite is fully immersed in water for rehydration.

37. A method according to claim 1, characterised in that the calcium sulphate anhydrite is fully immersed in a dilute salt solution for rehydration.

38. A method according to claim 37, characterised in that the salt solution comprises succinic acid.

39. A method according to claim 37, characterised in that the salt solution comprises potassium sulphate solution.

40. A method according to claim 1, characterised in that the concentration of the salt solution is about 0.1%.

41. A method according to claim 1, characterised in that finely powdered calcium sulphate di-hydrate is added to be present during rehydration such that the powdered calcium sulphate acts as crystal seeds.

42. A method according to claim 41, characterised in that addition is in the order of 5 g per liter of water.

43. A method according to claim 28, characterised in that the rehydration takes less than five days.

44. A method according to claim 1, characterised in that the subsequent calcium sulphate di-hydrate is dried following crystallisation.

45. A method according to claim 8, characterised in that the subsequent calcium sulphate di-hydrate is held in a damp condition prior to calcining.

46. A method of producing surgical grade calcium sulphate characterised in that the method comprises: forming an initial calcium sulphate di-hydrate from synthetic constituents; dehydrating the initial calcium sulphate di-hydrate to form calcium sulphate anhydrite; and subsequently rehydrating the calcium sulphate anhydrite by immersing in an aqueous solution and allowing subsequent calcium sulphate di-hydrate to crystallise out, wherein said aqueous solution is a dilute salt solution where the concentration of the salt in the solution is less than 1%.

47. A method of producing surgical grade calcium sulphate characterised in that the method comprises: forming an initial calcium sulphate di-hydrate from synthetic constituents; dehydrating the initial calcium sulphate di-hydrate to form calcium sulphate anhydrite; and subsequently rehydrating the calcium sulphate anhydrite by immersing in water and allowing subsequent calcium sulphate di-hydrate to crystallise out.

* * * * *